United States Patent
Westmarland et al.

(10) Patent No.: US 10,996,189 B2
(45) Date of Patent: May 4, 2021

(54) METHOD OF VENTING OXYGEN SENSORS

(71) Applicant: HONEYWELL INTERNATIONAL INC., Morris Plains, NJ (US)

(72) Inventors: Paul Westmarland, Morris Plains, NJ (US); Andy Millar, Morris Plains, NJ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 13 days.

(21) Appl. No.: 16/471,143

(22) PCT Filed: Dec. 19, 2016

(86) PCT No.: PCT/US2016/067515
§ 371 (c)(1),
(2) Date: Jun. 19, 2019

(87) PCT Pub. No.: WO2018/118005
PCT Pub. Date: Jun. 28, 2018

(65) Prior Publication Data
US 2020/0033289 A1    Jan. 30, 2020

(51) Int. Cl.
*G01N 27/404*    (2006.01)
(52) U.S. Cl.
CPC .................. *G01N 27/404* (2013.01)
(58) Field of Classification Search
None
See application file for complete search history.

(56) References Cited

U.S. PATENT DOCUMENTS

2012/0153942 A1    6/2012   Van et al.

FOREIGN PATENT DOCUMENTS

| CN | 1790001 A | 6/2006 |
|----|-----------|--------|
| CN | 102597761 A | 7/2012 |
| EP | 0298570 A2 | 1/1989 |
| EP | 2871472 A1 | 5/2015 |
| GB | 2326481 A | 12/1998 |
| WO | 1995/022055 A1 | 8/1995 |

OTHER PUBLICATIONS

Communication for European Application No. 16822872.4, dated Jul. 26, 2019, 3 pages.
International Search Report and Written Opinion for Application No. PCT/US2016/067515, dated Sep. 15, 2017, 10 pages.
Office Action issued in Chinese Application No. 201680091142.0 dated Nov. 4, 2020, 8 pages.

*Primary Examiner* — J. Christopher Ball
(74) *Attorney, Agent, or Firm* — Alston & Bird LLP

(57) ABSTRACT

A gas detector comprising a sensor (100) configured to detect the oxygen content in the ambient air around the gas detector; a housing configured to seal around a portion of the sensor, creating a hermetically sealed interior of the housing while exposing at least a portion of the sensor on the exterior of the housing; and a pressure equalizing element (112, 114) located between the exposed portion of the sensor and the hermetically sealed interior of the housing, configured to allow pressure equalization of the sealed interior of the housing.

19 Claims, 5 Drawing Sheets

METHOD OF VENTING OXYGEN SENSORS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Electrochemical gas sensors generally comprise electrodes in contact with an electrolyte for detecting a gas concentration. The electrodes are electrically coupled to an external circuit though lead wires that are coupled to connector pins. When a gas contacts the electrolyte and the electrodes, a reaction can occur that can create a potential difference between the electrodes or cause a current to flow between the electrodes. The resulting signal can be correlated with a gas concentration in the environment.

In some instances, the sensors can be used to detect a concentration of oxygen in an environment adjacent to the sensor over a range of environmental conditions. Electrochemical sensors such as oxygen sensors can experience a number of issues during operation, due to changes in pressure, temperature, gas content within the sensor.

SUMMARY

In an embodiment, a method for oxygen detection may comprise attaching a pressure equalizing element to the top surface of a sensor; installing the sensor onto a gas detector; sealing a housing of the gas detector around the sensor, wherein at least a portion of the pressure equalizing element is exposed on the exterior of the housing, and wherein at least a portion of the pressure equalizing element is located within the interior of the sealed housing; and equalizing the pressure within the sealed housing with the external pressure via the pressure equalizing element.

In an embodiment, a gas detector may comprise a sensor configured to detect the oxygen content in the ambient air around the gas detector; a housing configured to seal around a portion of the sensor, creating a hermetically sealed interior of the housing while exposing at least a portion of the sensor on the exterior of the housing; and a pressure equalizing element located between the exposed portion of the sensor and the hermetically sealed interior of the housing, configured to allow pressure equalization of the sealed interior of the housing.

In an embodiment, an oxygen sensor for use in a gas detector, the oxygen sensor may comprise a sensor housing comprising an opening allowing gas to enter the sensor; a plurality of electrodes within the sensor housing, wherein the plurality of electrodes comprise a working electrode and a counter electrode; and a pressure equalizing element comprising a first section located over the opening of the sensor and a second section located along the side of the sensor, wherein, when the sensor is assembled within the gas detector, the first section of the pressure equalizing element is located on the exterior of the gas detector, and the second section of the pressure equalizing element is located on the interior of the gas detector.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1A:
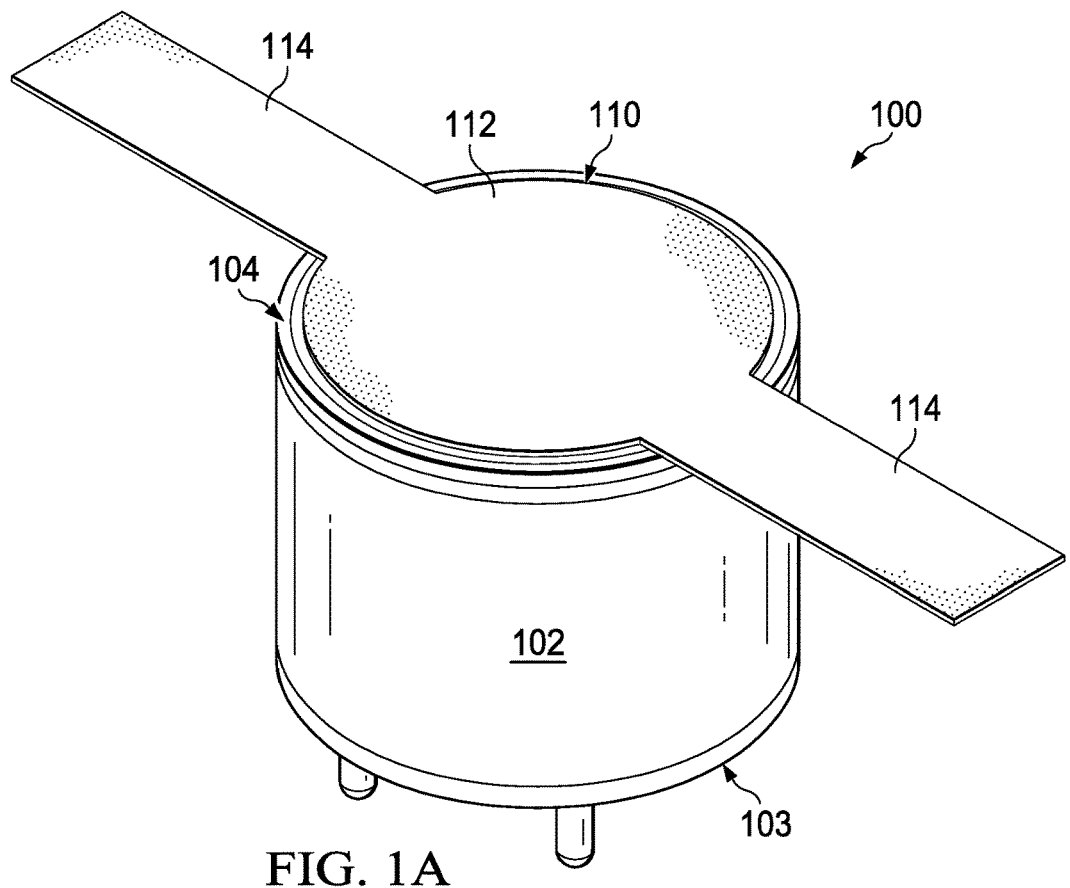
FIGS. 1A-1B illustrates a sensor for use in a gas detector according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for gas detection. Gas detectors may comprise one or more sensors configured to detect a particular gas in the ambient air around the gas detector.

Particularly, oxygen sensors (such as oxygen pumps or consumable anode oxygen sensors) often have a vent to minimize pressure differentials that can develop across the internal parts of the sensor, such as wetted separators. Without the vents, effects known as 'glitching' can occur when the sensor is exposed to temperature or pressure changes. Additionally, oxygen pumps may utilize a vent to exhaust oxygen that may be generated at the counter electrode of the sensor. It is often convenient, from a design point of view, for the vent to be in the base of the sensor. When the sensor is installed within a gas detector, the sensor may vent into the body or housing of the gas detector, rather than to the outside air. As a result it may be necessary for the gas detector itself to be vented to the outside air, both to ensure evolved oxygen does not build up within the gas detector and to avoid pressure differentials being built up across the sensor. Not all gas detectors have such a vent within the housing, and it may be undesirable for the gas detectors to be modified to accommodate vented sensors or oxygen pumps.

Embodiments of the disclosure may comprise an additional component on the top of the sensor configured to allow venting between the internal volume of the gas detector and the outside air (e.g., between an interior of a gas detector housing and the external environment), without compromising the watertight nature of the gas detector. This element may be called a pressure equalizing element. The pressure equalizing element may comprise a porous tape which fits over the top of the sensor instead of (or in addition to) an existing dust cover. The pressure equalizing element may comprise one or more sections (such as tabs) configured to extend from the top of the sensor into the interior of the gas detector, thereby providing a path for gas to provide pressure equalization between the interior of the gas detector and the exterior via an existing opening in the housing for the sensor.

Figure 1B:
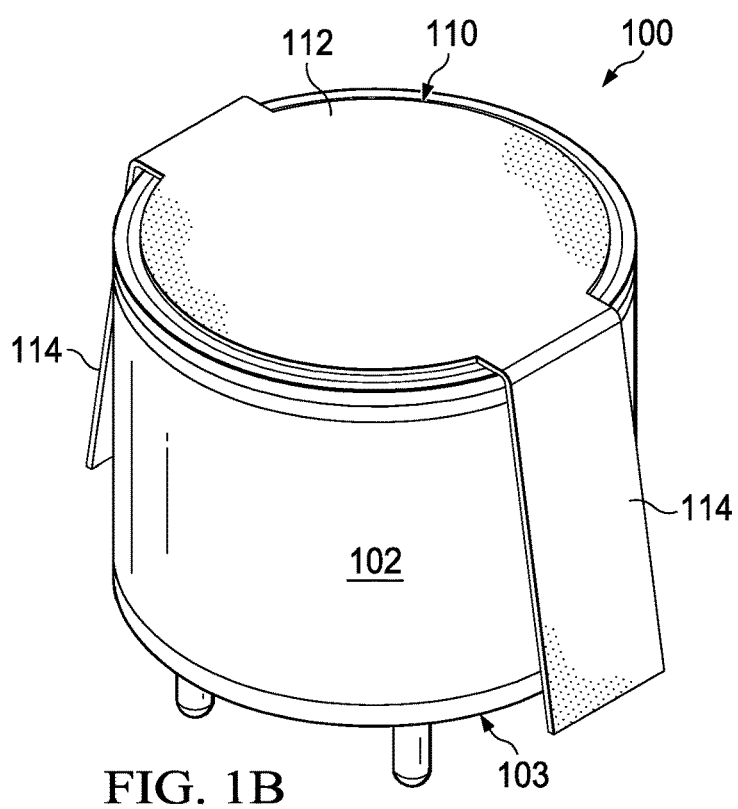

Referring now to FIGS. 1A-1B, an exemplary sensor 100 is shown, where the sensor 100 comprises a sensor housing 102 with an opening 104 on the top surface of the sensor housing 102. The opening 104 may allow gas from the environment to enter the sensor 100 (thereby allowing the sensor 102 to detect a particular gas within the environment). In some embodiments, the sensor 100 may comprise an oxygen sensor, and may be configured to determine the oxygen content in the ambient air. As shown in FIG. 1A-1B, the sensor 100 may also comprise a pressure equalizing element 110. The pressure equalizing element 110 may comprise a first section 112 and one or more second sections 114. In the embodiment shown, the first section 112 may be shaped to fit over the opening 104 of the sensor housing 102. In some embodiments, the first section 112 may be circular shaped to match the shape of the sensor housing 102. In the embodiment shown in FIGS. 1A-1B, the second sections 114 may comprise one or more tabs extending from the first section 112. The section sections 114 may be configured to extend within a housing of a gas detector (as further described below). As shown in FIG. 1B, the first section 112 of the pressure equalizing element 110 may be located on the top surface of the sensor housing 102, while the section section(s) 114 may be folded down and located along the side surface(s) of the sensor housing 102. In some embodiments, the pressure equalizing element 110 may be sealed around the opening 104 of the sensor 100 via adhesive and/or heat sealing. Certain materials may be used for the pressure equalizing element 110 that may be heat sealed and still have gas flow through the material.

The opening 104 of the sensor 100 may allow sample gas to enter the sensor housing 102 to be "sensed" or detected by the sensor 100. Therefore, the sample gas may also pass through the pressure equalizing element 110 before entering the sensor body 102. However, the path length for the sample gas to enter the opening 104 may be much shorter than for gas that is vented from the sensor via the pressure equalizing element 110. The sample gas may only travel the thickness of the pressure equalizing element 110, whereas the vented gas may travel the lateral length of the pressure equalizing element 110, where the lateral length may be significantly greater than the thickness. Additionally, any oxygen (or other gas) flowing out of the sensor and/or gas detector via the pressure equalizing element may be negligible in volume, and therefore may not affect the sensor readings.

In some embodiments, the sensor 100 may comprise a vent 103 to exhaust oxygen that may be generated at the counter electrode of the sensor 100. It may be convenient, due to the configuration of the sensor 100, for the vent 103 to be located at or near the base of the sensor 100. When the sensor 100 is installed in a gas detector, the vent 103 may be located within the housing of the gas detector. The pressure equalizing element 110 may comprise a hydrophobic material.

Figure 2:
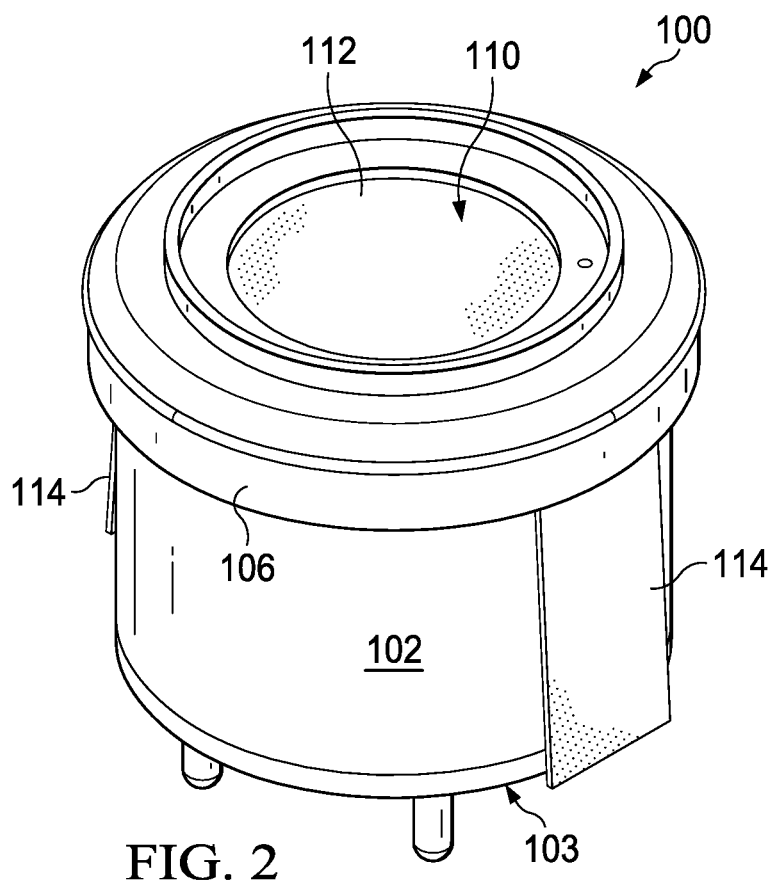
FIG. 2 illustrates another view of a sensor for use in a gas detector according to an embodiment of the disclosure.

Referring to FIG. 2, in some embodiments, a cap 106 may be fitted onto the sensor housing 102, where the cap 106 may attach and retain the pressure equalizing element 110 to the sensor 100. In some embodiments, the cap 106 may be sealed around the opening 104 of the sensor 100 via adhesive and/or heat sealing.

Figure 3:
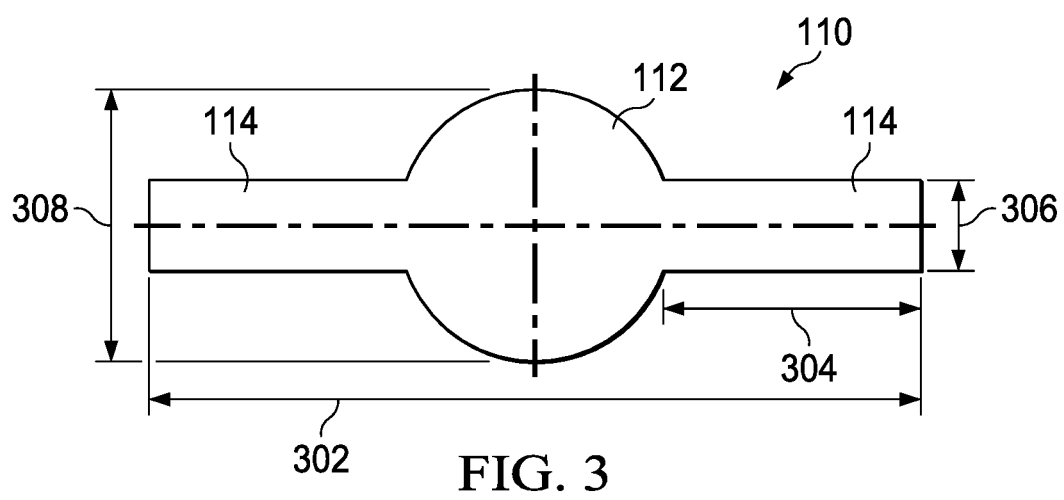
FIG. 3 illustrates a pressure equalizing element according to an embodiment of the disclosure.

Referring to FIG. 3, an exemplary diagram of a pressure equalizing element 110 is shown. In general, the pressure equalizing element 110 can be sized to cover the top of a gas sensor while having the second section 114 extend around a perimeter of the gas sensor. This can allow the pressure equalizing element 110 to be sealed around an opening in the gas detector while allowing the second section 114 to extend into an interior of the housing and provide a gas path between the interior of the housing and an external environment.

In an embodiment of the pressure equalizing element 110, the total length 302 of the element may be approximately 51 millimeters (mm). In an embodiment of the pressure equalizing element 110, the length 304 of a second section 114 may be approximately 17 mm. In an embodiment of the pressure equalizing element 110, the width 306 of a second section 114 may be approximately 6 mm. In an embodiment of the pressure equalizing element 110, the diameter 308 of the first section 112 may be approximately 18 mm.

The dimensions listed above may be one example, and the pressure equalizing element 110 may be sized and shaped to fit the sensor to which it is attached. Any dimensions or shapes may be included in this disclosure, while the pressure equalizing element is located at least partially within the housing of the gas detector, and at least partially outside the housing of the gas detector.

In some embodiments, the pressure equalizing element 110 may comprise a porous material. In some embodiments, the pressure equalizing element 110 may comprise a water resistant material. The water resistance of the pressure equalizing element 110 may allow the material to serve as a water barrier between an exterior environment and an interior of the gas detector such that gas detector maintains a water resistance, while still providing a gas path between an interior and exterior of the gas detector.

In some embodiments, the pressure equalizing element 110 may comprise Polytetrafluoroethylene (PTFE) material. In some embodiments, the pressure equalizing element 110 may comprise a porous material that allows gas flow through the material. In some embodiments, the pressure equalizing element 110 may comprise a typical airflow (through the material) of approximately 7 to 14 liters/hour/cm$^2$. In some embodiments, the pressure equalizing element 110 may comprise a material with a sufficient water ingress pressure (WIP), i.e. sufficiently high, to maintain the ingress protection rating of the instrument. In other words, the pressure equalizing element 110 may contribute to the water resistance of the entire sensor 100 as well as any other device into which the sensor 100 may be incorporated.

Figure 4:
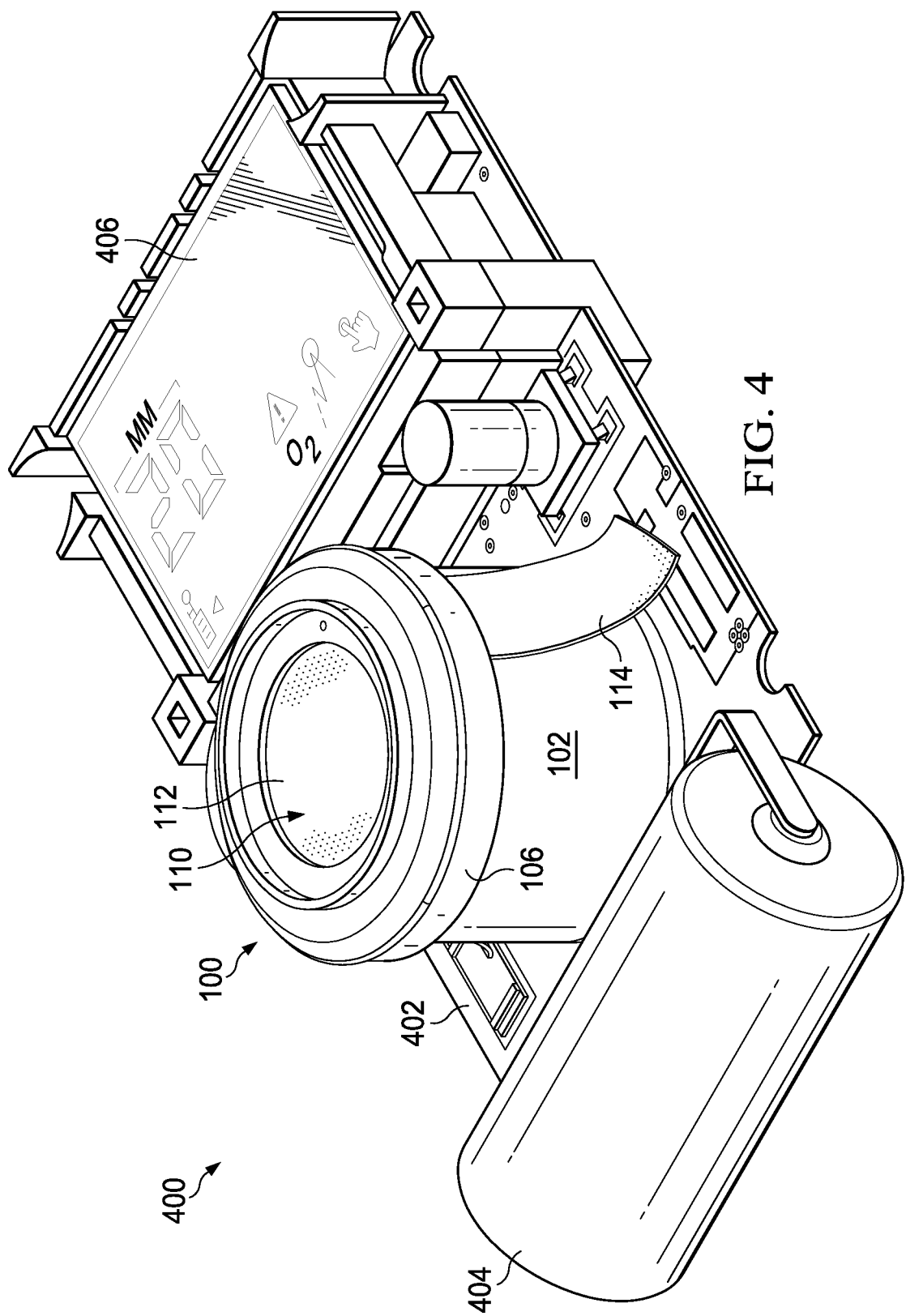
FIG. 4 illustrates a perspective view of a gas detector according to an embodiment of the disclosure.
Figure 5:
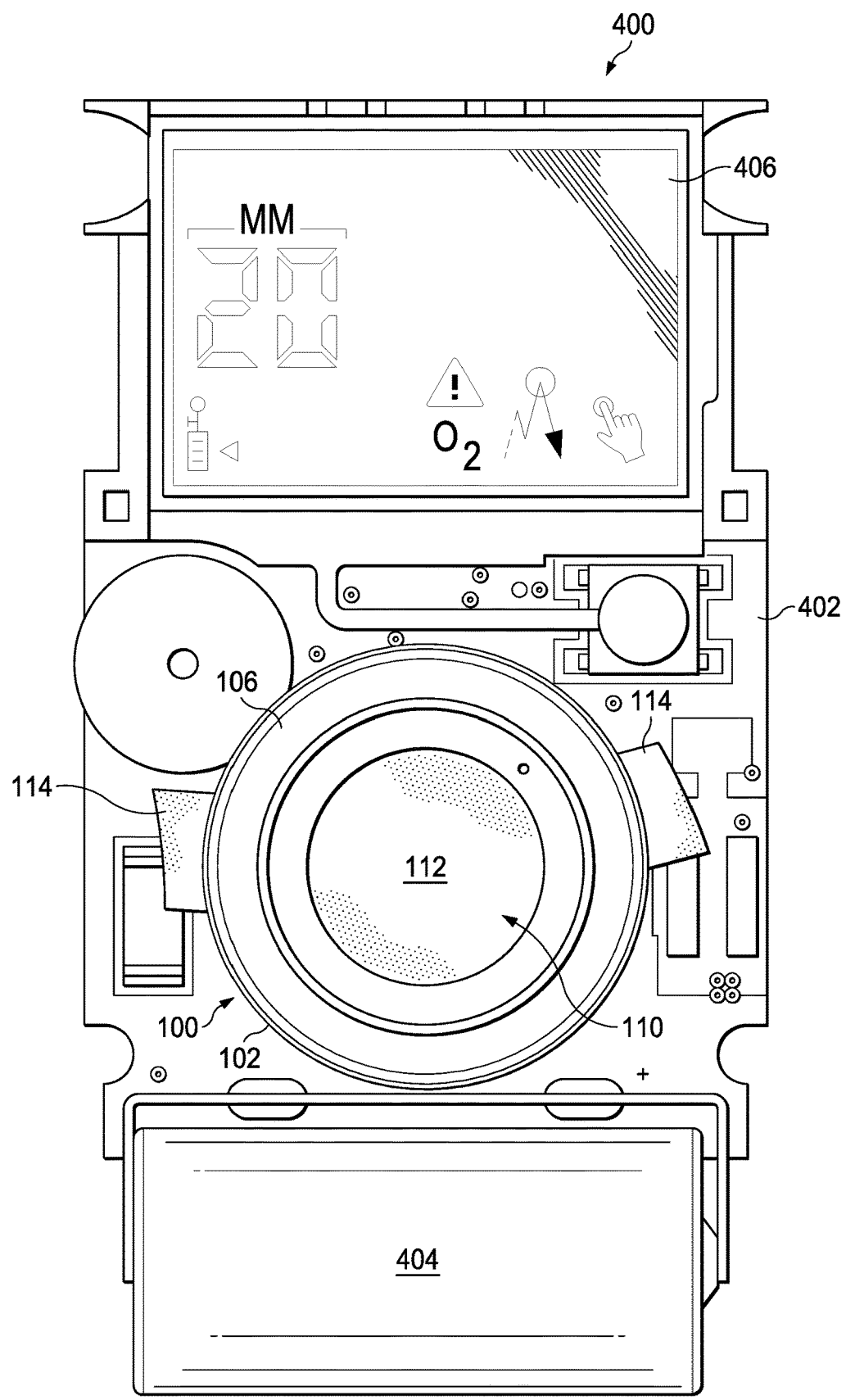
FIG. 5 illustrates a front view of a gas detector according to an embodiment of the disclosure.

Referring to FIGS. 4 and 5, the sensor 100 is shown attached to other elements of a gas detector 400. The gas detector 400 may comprise a power source, such as a battery 404. The gas detector 400 may comprise a controller, such as a printed circuit board (PCB) 402. The gas detector 400 may comprise a user interface, such as a display 406.

In some embodiments, the sensor 100 may be attached to (or at least in communication with) the controller 402. The top surface of the sensor 100 may be located opposite the attachment with the controller 402. The first section 112 of the pressure equalizing element 110 may be exposed by the cap 106. The second section(s) 114 of the pressure equalizing element 110 may be located beneath the cap 106 and extend from the cap 106 down the sides of the sensor housing 102.

Figure 6:
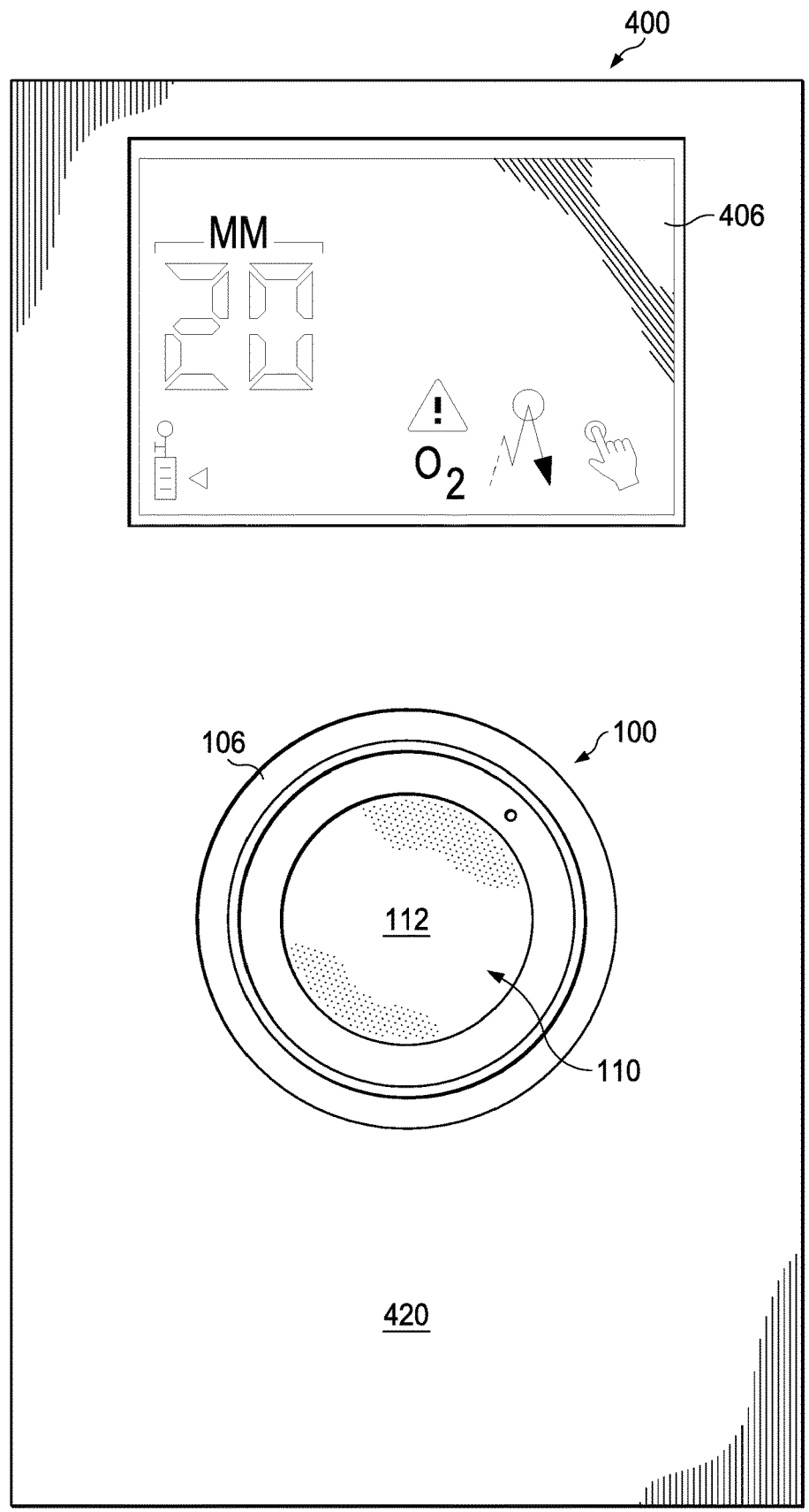
FIG. 6 illustrates another front view of a gas detector according to an embodiment of the disclosure.

Referring to FIG. 6, the elements of the gas detector 400 shown in FIGS. 4 and 5 may be covered by a housing 420. The housing 420 may be configured to seal around the sensor 100, exposing the top surface of the sensor 100. In some embodiments, the housing 420 may seal with the cap 106 of the sensor 100. The housing 420 may be configured to form a water resistant seal around the other elements of the gas detector 400, thereby protecting the gas detector 400 from water damage. In some embodiments, the housing 420 may seal around the user interface 406, allowing a user to access the user interface 406. As shown in FIG. 6, the first section 112 of the pressure equalizing element 110 may be exposed via the cap 106 when the housing 420 is in place, while the second section 114 (shown above) may be located within the interior of the housing 420.

The pressure equalizing element 110 may allow the pressure within the housing 420 to equalize with the pressure outside the housing 420 while the gas detector 400 is in use. The pressure within the housing 420 may change due to external pressure changes, temperature changes, humidity changes, and/or the generation of gas by the sensor 100 during use. For example, the vent 103 (shown above) of the sensor 100 may located within the housing 420, such that any gases that are vented from the sensor 100 are vented to the interior of the housing 420. Venting of the housing 420 may be achieved by gas flow through the pressure equalizing element 110. In some embodiments, the pressure equalizing element 110 may form the only gas path between an interior of the housing 420 and the exterior of the housing 420 such that the housing is otherwise sealed (e.g., forming a gas tight seal).

EXAMPLE

During testing of an exemplary gas detector 400 comprising a pressure equalizing element 110, the gas detector 400 was compared to a typical gas detector that did not comprise a pressure equalizing element. When both gas detectors were taken from room temperature (approximately 20° C.) to approximately −20° C., the gas detector comprising the pressure equalizing element did not initiate an alarm. However, the gas detector not comprising the pressure equalizing element initiated a high $O_2$ alarm (approximately 24% $O_2$ and then "Over Limit").

Similarly, when both gas detectors were returned to room temperature from −20° C., the gas detector comprising the pressure equalizing element did not initiate an alarm. However, the gas detector not comprising the pressure equalizing element initiated a low $O_2$ alarm (approximately 17% $O_2$).

This testing illustrates that the gas detector comprising the pressure equalizing element was able to accommodate for (and equalize) the pressure change that occurred within the housing of the gas detector due to the temperature change, while still maintaining accurate sensor readings.

Having described various devices and methods herein, exemplary embodiments or aspects can include, but are not limited to:

In a first embodiment, a method for oxygen detection may comprise attaching a pressure equalizing element to the top surface of a sensor; installing the sensor onto a gas detector; sealing a housing of the gas detector around the sensor, wherein at least a portion of the pressure equalizing element is exposed on the exterior of the housing, and wherein at least a portion of the pressure equalizing element is located within the interior of the sealed housing; and equalizing the pressure within the sealed housing with the external pressure via the pressure equalizing element.

A second embodiment can include the method of the first embodiment, further comprising allowing gas flow through the pressure equalizing element to equalize the pressure within the sealed housing.

A third embodiment can include the method of the first or second embodiments, wherein the pressure equalizing element comprises a first section and a second section, wherein the first section is located on the top surface of the sensor, and wherein the second section is located on a side surface of the sensor.

A fourth embodiment can include the method of any of the first to third embodiments, wherein attaching the pressure equalizing element to the top surface of the sensor comprises installing a cap over the pressure equalizing element and the top surface of the sensor.

A fifth embodiment can include the method of any of the first to fourth embodiments, further comprising venting the sensor into the sealed housing.

A sixth embodiment can include the method of any of the first to fifth embodiments, wherein the sensor comprises an oxygen sensor.

A seventh embodiment can include method of the sixth embodiment, further comprising venting oxygen generated at a counter electrode of the oxygen sensor into the sealed housing.

An eighth embodiment can include the method of any of the first to seventh embodiments, wherein the pressure equalizing element comprises a PTFE material.

In a ninth embodiment, a gas detector may comprise a sensor configured to detect the oxygen content in the ambient air around the gas detector; a housing configured to seal around a portion of the sensor, creating a hermetically sealed interior of the housing while exposing at least a portion of the sensor on the exterior of the housing; and a pressure equalizing element located between the exposed portion of the sensor and the hermetically sealed interior of the housing, configured to allow pressure equalization of the sealed interior of the housing.

A tenth embodiment can include the gas detector of the ninth embodiment, further comprising a cap configured to fit over the pressure equalizing element and a top surface of the sensor.

An eleventh embodiment can include the gas detector of the tenth embodiment, wherein the housing is configured to seal with the cap.

A twelfth embodiment can include the gas detector of any of the ninth to eleventh embodiments, wherein the pressure equalizing element comprises a first section located on the top surface of the sensor, and a second section located on a side surface of the sensor.

A thirteenth embodiment can include the gas detector of any of the ninth or twelfth embodiments, wherein the pressure equalizing element is configured to allow pressure equalization with or without bulk gas flow through the pressure equalizing element.

A fourteenth embodiment can include the gas detector of any of the ninth to thirteenth embodiments, wherein the sensor is configured to vent any gases generated within the sensor into the sealed housing, thereby creating a pressure differential between the interior and exterior of the housing.

A fifteenth embodiment can include the gas detector of any of the ninth to fourteenth embodiments, wherein the sensor comprises an oxygen sensor, and wherein oxygen generated at a counter electrode of the oxygen sensor is vented into the sealed housing.

In a sixteenth embodiment, an oxygen sensor for use in a gas detector, the oxygen sensor may comprise a sensor housing comprising an opening allowing gas to enter the sensor; a plurality of electrodes within the sensor housing, wherein the plurality of electrodes comprise a working electrode and a counter electrode; and a pressure equalizing element comprising a first section located over the opening of the sensor and a second section located along the side of the sensor, wherein, when the sensor is assembled within the gas detector, the first section of the pressure equalizing element is located on the exterior of the gas detector, and the second section of the pressure equalizing element is located on the interior of the gas detector.

A seventeenth embodiment can include the oxygen sensor of the sixteenth embodiment, wherein the pressure equalizing element is configured to allow pressure equalization between the interior of the gas detector and the exterior of the gas detector.

An eighteenth embodiment can include the oxygen sensor of the sixteenth or seventeenth embodiments, wherein the sensor is configured to vent oxygen generated at the counter electrode into the interior of the gas detector.

A nineteenth embodiment oxygen sensor of any of the sixteenth to eighteenth embodiments, wherein the pressure equalizing element comprises a PTFE material.

A twentieth embodiment can include the oxygen sensor of any of the sixteenth to eighteenth embodiments, further comprising a cap configured to fit over the opening of the sensor and the pressure equalizing element, attaching the pressure equalizing element to the sensor.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for oxygen detection comprising:
   exposing a gas detector comprising a sensor to an environment, wherein the gas detector comprises:
   a pressure equalizing element coupled to a top surface of the sensor;
   a housing, wherein the housing of the gas detector is sealed around the sensor, wherein at least a portion of the pressure equalizing element is exposed on an exterior of the housing, and wherein at least a portion of the pressure equalizing element is located within an interior of the housing;
   detecting a sample gas by the sensor, wherein the sample gas passes through a thickness of the pressure equalizing element into a sensor body;
   equalizing a pressure within the sealed housing with an external pressure of the environment via the pressure equalizing element, wherein gas flow travels a lateral length of at least a portion of the pressure equalizing element, and wherein the lateral length is greater than the thickness of the pressure equalizing element, and
   allowing pressure equalization, via the pressure equalizing element, with or without bulk gas flow through the pressure equalizing element.

2. The method of claim 1, wherein detecting the sample gas by the sensor comprises allowing the sample gas to enter the sensor body via an opening, and wherein the pressure equalizing element is sealed around the opening.

3. The method of claim 1, wherein the pressure equalizing element comprises a first section and a second section, wherein the first section is located on the top surface of the sensor, and wherein the second section is located on a side surface of the sensor.

4. The method of claim 1, wherein the gas detector comprises a cap disposed over the pressure equalizing element and the top surface of the sensor.

5. The method of claim 1, further comprising venting the sensor into the sealed housing.

6. The method of claim 1, wherein the sensor comprises an oxygen sensor.

7. The method of claim 6, further comprising venting oxygen generated at a counter electrode of the oxygen sensor into the sealed housing.

8. The method of claim 1, wherein the pressure equalizing element comprises a PTFE material.

9. A gas detector comprising:
   a sensor configured to detect oxygen content in ambient air around the gas detector, wherein a sample gas enters a sensor body via an opening;
   a housing configured to seal around a portion of the sensor, creating a hermetically sealed interior of the housing while exposing at least a portion of the sensor on an exterior of the housing; and
   a pressure equalizing element located between the exposed at least a portion of the sensor and the hermetically sealed interior of the housing, configured to:
   allow pressure equalization of the sealed interior of the housing, wherein the pressure equalizing element is sealed around the opening of the sensor body, and
   allow pressure equalization with or without bulk gas flow through the pressure equalizing element.

10. The gas detector of claim 9, further comprising a cap configured to fit over the pressure equalizing element and a top surface of the sensor.

11. The gas detector of claim 9, wherein the sample gas passes through a thickness of the pressure equalizing element into the sensor body, wherein vented gas flow travels a lateral length of at least a portion of the pressure equalizing element, and wherein the lateral length is greater than the thickness of the pressure equalizing element.

12. The gas detector of claim 9, wherein the pressure equalizing element comprises a first section located on a top surface of the sensor, and a second section located on a side surface of the sensor.

13. The gas detector of claim 9, wherein the sensor is configured to vent any gases generated within the sensor into the sealed housing, thereby creating a pressure differential between the interior and exterior of the housing.

14. The gas detector of claim 9, wherein the sensor comprises an oxygen sensor, and wherein oxygen generated at a counter electrode of the oxygen sensor is vented into the sealed housing.

15. An oxygen sensor for use in a gas detector, the oxygen sensor comprising:
   a sensor housing comprising an opening allowing gas to enter the sensor;
   a plurality of electrodes within the sensor housing, wherein the plurality of electrodes comprise a working electrode and a counter electrode; and
   a pressure equalizing element comprising a first section located over the opening of the sensor and a second section located along a side of the sensor, wherein, when the sensor is assembled within the gas detector, the first section of the pressure equalizing element is located on an exterior of the gas detector, and the second section of the pressure equalizing element is located on an interior of the gas detector, and wherein the pressure equalizing element is configured to allow pressure equalization with or without bulk gas flow through the pressure equalizing element.

16. The oxygen sensor of claim 15, wherein the pressure equalizing element is configured to allow pressure equalization between the interior of the gas detector and the exterior of the gas detector.

17. The oxygen sensor of claim 15, wherein the sensor is configured to vent oxygen generated at the counter electrode into the interior of the gas detector.

18. The oxygen sensor of claim 15, wherein the pressure equalizing element comprises a PTFE material.

19. The oxygen sensor of claim 15, further comprising a cap configured to fit over the opening of the sensor and the pressure equalizing element, attaching the pressure equalizing element to the sensor.

* * * * *